(12) United States Patent
Moraitis

(10) Patent No.: US 12,102,642 B2
(45) Date of Patent: *Oct. 1, 2024

(54) TREATMENT OF HYPERCOAGULOPATHY IN CUSHING'S SYNDROME BY ADMINISTRATION OF GLUCOCORTICOID RECEPTOR MODULATORS

(71) Applicant: Corcept Therapeutics Incorporated, Menlo Park, CA (US)

(72) Inventor: Andreas G. Moraitis, Sunny Isles Beach, FL (US)

(73) Assignee: Corcept Therapeutics Incorporated, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/983,971

(22) Filed: Nov. 9, 2022

(65) Prior Publication Data

US 2023/0097191 A1    Mar. 30, 2023

Related U.S. Application Data

(63) Continuation of application No. 16/723,626, filed on Dec. 20, 2019, now Pat. No. 11,524,013.
(Continued)

(51) Int. Cl.
*A61K 31/567* (2006.01)
*A61P 7/04* (2006.01)
*G01N 33/74* (2006.01)

(52) U.S. Cl.
CPC .............. *A61K 31/567* (2013.01); *A61P 7/04* (2018.01); *G01N 33/743* (2013.01)

(58) Field of Classification Search
CPC ........ A61K 31/567; A61P 7/04; G01N 33/743
(Continued)

(56) References Cited

U.S. PATENT DOCUMENTS 10,604,807 B2    3/2020   Belanoff et al.
11,058,670 B2 *  7/2021   Moraitis .............. A61K 31/437
(Continued)

FOREIGN PATENT DOCUMENTS

CN    108014108 A    5/2018
CN    113490496 A    10/2021
WO    2017027851      2/2017

OTHER PUBLICATIONS

FDA Prescribing Information for Korlym™ (Mifepristone) 300 mg tablet, FDA, Published Feb. 2012, pp. 1-23 (Year: 2012).*
(Continued)

*Primary Examiner* — Jeffrey S Lundgren
*Assistant Examiner* — Heather Dahlin
(74) *Attorney, Agent, or Firm* — Kilpatrick Townsend & Stockton LLP

(57) ABSTRACT

Novel methods for preventing, reducing the risk of development of, and for treating hypercoagulopathy in Cushing's syndrome patients with elevated risk of developing hypercoagulopathy are disclosed. The methods are further useful to prevent, to reduce the risk of developing, and to treat deep vein thrombosis (DVT), pulmonary embolism (PE), and venous thromboembolism (VTE); and to treat inflammatory states.
The methods include: administering heteroaryl-ketone fused azadecalin glucocorticoid receptor modulator (HKGRM) to a Cushing's syndrome patient at risk of developing hypercoagulopathy, thereby treating hypercoagulopathy. Methods of preventing, reducing risk of developing, and of treating DVT, PR, or VTE in a Cushing's syndrome patient comprise administering a HKGRM to the patient. Methods of unmasking and subsequently reducing an inflammatory state comprise administering an effective amount of a HKGRM to a Cushing's syndrome patient, effective first to increase
(Continued)

inflammatory symptoms and then to subsequently decrease said inflammatory symptoms in the patient.

10 Claims, 6 Drawing Sheets

Related U.S. Application Data

(60) Provisional application No. 62/784,270, filed on Dec. 21, 2018.

(58) Field of Classification Search
USPC .......................................................... 514/170
See application file for complete search history.

(56) References Cited

U.S. PATENT DOCUMENTS

| | | | |
|---|---|---|---|
| 11,268,145 | B2 | 3/2022 | Belanoff et al. |
| 11,524,013 | B2 * | 12/2022 | Moraitis .............. A61K 31/567 |
| 11,590,113 | B2 * | 2/2023 | Moraitis .............. A61K 31/437 |
| 11,684,612 | B2 * | 6/2023 | Moraitis .............. A61K 31/437 |
| 2010/0261693 | A1 | 10/2010 | Ulmann et al. |
| 2014/0038926 | A1 | 2/2014 | Hunt et al. |
| 2016/0067264 | A1 | 3/2016 | Newell-Price |

OTHER PUBLICATIONS

Hunt HJ, Belanoff JK, Walters I, Gourdet B, Thomas J, Barton N, Unitt J, Phillips T, Swift D, Eaton E. Identification of the clinical candidate . . . (CORT125134): a selective glucocorticoid receptor (GR) antagonist. Journal of Medicinal Chemistry. Apr. 27, 2017;60(8):3405-21. (Year: 2017).*
Hunt HJ et al. Identification of the clinical candidate . . . (CORT125134): a selective glucocorticoid receptor (GR) antagonist. Journal of Medicinal Chemistry. Apr. 27, 2017;60(8):3405-21. (Year: 2017).*
Nieman LK, Biller BM, Findling JW, Murad MH, Newell-Price J, Savage MO, Tabarin A. Treatment of Cushing's syndrome: an endocrine society clinical practice guideline. The Journal of Clinical Endocrinology & Metabolism. Aug. 1, 2015; 100(8):2807-31. (Year: 2015).*
Hunt H, Donaldson K, et al. Assessment of safety, tolerability, pharmacokinetics, and pharmacological effect of orally administered CORT125134: an adaptive, double-blind, randomized, placebo-controlled phase 1 clinical study. Clinical pharmacology in drug development. May 2018;7(4):408-21. (Year: 2018).*
Van der Pas, et al. "The hypercoagulable state in Cushing's disease is associated with increased levels of procoagulant factors and impaired fibrinolysis, but is not reversible after short-term biochemical remission induced by medical therapy." The J. of Clinical Endo & Met. 97.4 (2012): 1303-1310 (Year: 2012).*
Park, F. M., et al. "Hypercoagulability and ACTH-dependent hyperadrenocorticism in dogs." Journal of Veterinary Internal Medicine 27.5 (2013): 1136-1142. (Year: 2013).*
Lopes V, Marques O, De Sousa Lages A. Preventive strategies for hypercoagulation in Cushing's syndrome: when and how. Thrombosis Journal. Jul. 3, 2023;21(1):72. (Year: 2023).*
Casonato et al., "Abnormalities of Von Willebrand Factor are also Part of the Prothrombotic State of Cushing's Syndrome", Blood Coagulation and Fibrinolysis, vol. 10, No. 3, Feb. 11, 1999, pp. 145-151.
EP19898016.1 , "Extended European Search Report", Aug. 8, 2022, 9 pages.
Ferrau et al., "Metabolic Syndrome in Cushing's Syndrome Patients", Frontiers of Hormone Research, vol. 49, Apr. 2018, pp. 85-103.
Herkert et al., "Sex Steroids Used in Hormonal Treatment Increase Vascular Procoagulant Activity by Inducing Thrombin Receptor (PAR-1) Expression: Role of the Glucocorticoid Receptor", Circulation, vol. 104, No. 23, Dec. 4, 2001, pp. 2826-2831.
Hunt et al., "Assessment of Safety, Tolerability, Pharmacokinetics, and Pharmacological Effect of Orally Administered CORT125134: An Adaptive, Double-Blind, Randomized, Placebo-Controlled Phase 1 Clinical Study", Clinical Pharmacology in Drug Development, vol. 7, No. 4, May 2018, pp. 408-421.
Nakashima et al., "Hypercoagulable States: an Algorithmic Approach to Laboratory Testing and Update on Monitoring of Direct Oral Anticoagulants", Blood Research, vol. 49, No. 2, Jun. 2014, pp. 85-94.
PCT/US2019/067894 , "International Search Report and Written Opinion", Apr. 23, 2020, 11 pages.
Sharma et al., "Comorbidities in Cushing's Disease", Pituitary, vol. 18, 2015, pp. 188-194.
Stuijver et al., "Incidence of Venous Thromboembolism in Patients with Cushing's Syndrome: A Multicenter Cohort Study", The Journal of Clinical Endocrinology & Metabolism, vol. 96, No. 11, Nov. 1, 2011, pp. 3525-3532.
Trementino et al., "Coagulopathy in Cushing's Syndrome", Neuroendocrinology, vol. 92, No. 1, Sep. 10, 2010, pp. 55-59.
Van Der Pas et al., "Hypercoagulability In Cushing's Syndrome: Prevalence, Pathogenesis and Treatment", Clinical Endocrinology, vol. 78, No. 4, Apr. 2013, pp. 481-488.
Webb et al., "Morbidity of Cushing's Syndrome and Impact of Treatment", Endocrinology & Metabolism Clinics of North America, vol. 47, No. 2, Apr. 9, 2018, pp. 299-311.
U.S. Appl. No. 16/723,626 , "Non-Final Office Action", Jul. 7, 2022, 25 pages.
U.S. Appl. No. 16/723,626 , "Notice of Allowance", Oct. 17, 2022, 8 pages.
Chinese Patent Application No. 201980084234.X , "Office Action", Jun. 7, 2024, 8 pages.

* cited by examiner

TREATMENT OF HYPERCOAGULOPATHY IN CUSHING'S SYNDROME BY ADMINISTRATION OF GLUCOCORTICOID RECEPTOR MODULATORS

CROSS-REFERENCE TO RELATED APPLICATIONS

This application is a continuation of U.S. application Ser. No. 16/723,626, filed Dec. 20, 2019, which claims the benefit of, and priority to, U.S. Patent Application 62/784,270, filed Dec. 21, 2018, the contents of which are is hereby incorporated by reference in their entirety.

BACKGROUND

The coagulation of blood is a vital capability required for health, being critical for wound repair, for avoidance of hemorrhage, and for other reasons. Paucity or lack of one or more factors responsible for blood clotting is the cause of hemophilia, a serious inherited disorder. However, blood hypercoagulability (excess propensity of the blood to coagulate) can lead to significant, and sometimes life-threatening conditions, including intravenous and intraarterial blood clots (thrombi) which may lead to embolisms and strokes (a stroke occurs when an embolism lodges in the brain vasculature, cutting off blood supply to regions of the brain downstream of the clot). The formation or presence of a thrombus in the deep veins, typically in the legs, although such thrombi may form in the upper extremities as well, is termed deep vein thrombosis (DVT). A pulmonary embolism (PE) is caused by an obstruction of a pulmonary artery or branches thereof; such emboli are often caused by thrombi that originally formed in a deep vein. The combination of DVT and PE is termed venous thromboembolism (VTE), and is a serious condition. Cushing's syndrome is a disorder in which excessive blood clotting may be exhibited.

Hypercortisolism, often referred to as Cushing's syndrome, is caused by excessive activity of the stress hormone cortisol. Where Cushing's syndrome is caused by administration of glucocorticoid (GC) drugs, it is termed "exogenous Cushing's syndrome"; cases in which the excess cortisol is produced by the patient are termed "endogenous Cushing's syndrome". Endogenous Cushing's syndrome is often caused by a pituitary tumor (typically an adenoma), and is then termed Cushing's Disease. Cases of endogenous Cushing's syndrome that are caused by non-pituitary sources of cortisol are termed "ectopic Cushing's syndrome". Endogenous Cushing's syndrome is an orphan disease that most often affects adults aged 20-50. In the United States, an estimated 20,000 patients have Cushing's syndrome, with about 3,000 new patients being diagnosed each year. Symptoms vary, but most people experience one or more of the following manifestations: high blood sugar (hyperglycemia), diabetes, high blood pressure, upper-body obesity, rounded face, increased fat around the neck, thinning arms and legs, easy bruising, facial plethora, acne, red purple stripes across the body, severe fatigue and weak muscles. Irritability, anxiety, cognitive disturbances and depression are also common. Cushing's syndrome can affect every organ system in the body and can be lethal if not treated effectively. One cause of death in Cushing's syndrome patients is due to emboli caused by hypercoagulopathy associated with the syndrome. Hypercoagulopathy is associated with, and may cause, emboli associated with arterial thrombosis or venous thromboembolism (VTE), including pulmonary emboli and deep vein thrombosis. Such emboli may occur and are often fatal. Stroke is another common result of emboli due to hypercoagulopathy.

Cushing's syndrome patients may be treated surgically to remove, as much as possible, the source of the excess cortisol, and by other means. Cushing's syndrome patients may receive medical treatment, such as by administration of glucocorticoid receptor modulators, such as mifepristone, to reduce or block the effects of excess cortisol (see, e.g., U.S. Pat. Nos. 9,943,526; 9,956,216, both of which patents are hereby incorporated by reference in their entireties). However, the hypercoagulopathy experienced by Cushing's syndrome patients often persists following surgery for Cushing's syndrome. The coagulation factors Factor VIII and von Willebrand Factor increased one month after surgery, and took six months or more to decline below the levels found prior to surgery (Casonato, et al. Blood Coagulation and Fibrinolysis 10(3):145-151 (1999)).

Accordingly, methods for treating Cushing's syndrome patients in order to reduce the risk of developing hypercoagulopathy, DVT, PE, VTE, or other embolic disorder are lacking in the art and are required.

SUMMARY

Applicant provides novel methods for preventing or treating hypercoagulopathy. In embodiments, these novel methods are effective for preventing or treating hypercoagulopathy in Cushing's syndrome patients at risk of, or suffering from, a disease or condition associated with an elevated risk of developing hypercoagulopathy, or from a disease or condition associated with an elevated risk of developing deep vein thrombosis (DVT), pulmonary embolism (PE), and venous thromboembolism (VTE). In embodiments, these novel methods are effective for treating an inflammatory state in Cushing's syndrome patients suffering from a disease or condition associated with an elevated risk of developing hypercoagulopathy, or from a disease or condition associated with an elevated risk of developing DVT, PE, and VTE. In embodiments, these novel methods are effective for unmasking an inflammatory state in Cushing's syndrome patients suffering from, or at risk of developing, hypercoagulopathy, DVT, PE, or VTE.

In embodiments, the methods comprise prophylactic methods suitable for, and effective for, reducing the risk of development of hypercoagulopathy in Cushing's syndrome patients. In embodiments, the methods comprise prophylactic methods suitable for, and effective for, reducing the risk of development of DVT, PE, and VTE in Cushing's syndrome patients.

In embodiments, Applicant discloses herein methods of treating hypercoagulopathy in a patient suffering from Cushing's syndrome, comprising: Administering an effective amount of a glucocorticoid receptor modulator (GRM) to said patient, whereby said hypercoagulopathy is treated. In embodiments, the methods of treating hypercoagulopathy in a patient suffering from Cushing's syndrome further comprise determining that the Cushing's syndrome patient is suffers from, or is at elevated risk of developing, hypercoagulopathy. In embodiments, the GRM is a glucocorticoid receptor antagonist (GRA). In embodiments, the GRM is mifepristone. In embodiments, the GRM or GRA is a heteroaryl-ketone fused azadecalin GRM (HKGRM). In embodiments, the HKGRM is relacorilant.

In embodiments, Applicant discloses herein methods of reducing the risk of developing DVT, PE, or VTE in a patient suffering from Cushing's syndrome, comprising: Administering a medical treatment for Cushing's syndrome, said medical treatment comprising administering an effective amount of a glucocorticoid receptor modulator (GRM) to said patient, Whereby said risk of developing DVT, PE, or VTE is reduced as compared to the risk of developing DVT, PE, or VTE in a Cushing's patient who had not previously received said medical treatment for Cushing's syndrome. In embodiments, the risk of developing DVT, PE, or VTE in the Cushing's syndrome patient is reduced at one month of medical treatment as compared to the risk, one month following surgery, of developing DVT, PE, or VTE in a Cushing's patient who has received surgical treatment for Cushing's syndrome. In embodiments, the methods of reducing the risk of developing DVT, PE, or VTE in a patient suffering from Cushing's syndrome further comprise determining that the Cushing's syndrome patient is suffers from, or is at elevated risk of developing, hypercoagulopathy.

In embodiments, Applicant discloses herein methods of unmasking and subsequently reducing an inflammatory state in a patient suffering from Cushing's syndrome, comprising: Administering an effective amount of a GRM to said patient, Effective to increase inflammatory symptoms in said patient within about 4 weeks of beginning said administration, and Effective to subsequently decrease said inflammatory symptoms in said patient by about 3 to 4 months after beginning said administration, Whereby said inflammatory state is reduced in Cushing's syndrome. In embodiments of the methods of unmasking and subsequently reducing an inflammatory state in a patient suffering from Cushing's syndrome, the inflammatory symptoms comprise greater than normal C-Reactive protein levels. In embodiments, the methods of unmasking and subsequently reducing an inflammatory state in a patient suffering from Cushing's syndrome further comprise determining that the Cushing's syndrome patient suffers from, or is at elevated risk of developing, hypercoagulopathy.

In embodiments of the methods disclosed herein, the GRM is a heteroaryl ketone fused azadecalin GRM, and may be relacorilant. In embodiments of the methods disclosed herein, the GRM is a steroidal GRM, and may be mifepristone.

Applicant discloses herein that the coagulation profile of the Cushing's patients treated with relacorilant was improved compared to baseline. In contrast to prior observations of Cushing's syndrome patients treated surgically, relacorilant administration did not lead to an increase in either Factor VIII or von Willebrand's Factor, and declined with only a few months of relacorilant treatment. APTT measurements increased in Cushing's patients receiving relacorilant, indicating that the risk of coagulation and of risk of DVT, PE, and VTE was reduced. These results show that relacorilant treatment improves the coagulation profile of Cushing's patients. These results further suggest that relacorilant treatment of Cushing's patients provides a better coagulation factor profile, earlier after treatment, than does surgery.

Accordingly, Applicant provides herein methods to treat hypercoagulopathy seen in Cushing's syndrome patients in a way that is much safer than surgery. The acute decreases of cortisol activity or cortisol levels associated with successful surgery for Cushing's syndrome poses the risk of worsening hypercoagulopathy in the post-operative period—up to about 4 months—due to the effect of underlying inflammation that is suppressed by cortisol excess and flares upon successful surgery. Gradual treatment of the chronic cortisol excess, provided by the methods disclosed herein, prevents the acute exacerbation of occult inflammation and improves the coagulation profile in patients at high risk for DVT, PE, and VTE.

Comparing the coagulation factor changes following successful Cushing's syndrome surgery with those in patients treated medically with a GRM it becomes obvious that the two main coagulation factors associated with steroid induced hypercoagulaopthy (factor VIII and VWF) are gradually decreasing with medical treatment, while in patients undergoing surgery both of those factors increase post operatively and remain elevated for at least one month post-operative (Casonato, et al. Blood Coagulation and Fibrinolysis 10(3):145-151 (1999)). That also agrees with the observation of increased risk of DVT, PE, and VTE following successful treatment of Cushing's syndrome and the Cushing's syndrome treatment guidelines which recommend use of anti-coagulation for at least 3 months following successful surgery. Thus, the present GRM treatments provide advantages over surgical treatments.

When used as the sole treatment for hypercoagulopathy; or for treating DVT, PE, or VTE; or for unmasking and treating inflammatory states, the present methods are believed to provide better treatments as compared to previous surgical or medical treatments for the conditions underlying hypercoagulopathy; risk of DVT, PE, or VTE; and inflammatory states. When used in conjunction with other treatments, the present methods are believed to act synergistically with such other treatments to provide more effective treatment for hypercoagulopathy; risk of DVT, PE, or VTE; and inflammatory states than would be provided by the other treatments alone. The methods disclosed herein provide advantages of treating hypercoagulopathy, DVT, PE, VTE, and inflammatory states in a Cushing's syndrome patient, either by administration of a GRM alone, or, when administered in conjunction with a second anticoagulation therapy, by adding to and improving the prior therapy. The methods disclosed herein are believed to provide treatments which result in outcomes at least as favorable as, or better than, outcomes resulting from surgical procedures, yet which do not require surgery, and are available to patients unable or unwilling to undergo surgery, or for whom surgery proved to be incompletely successful or unsuccessful.

Other objects, features, and advantages of the methods disclosed herein will be apparent to one of skill in the art from the following detailed description and figures.

DETAILED DESCRIPTION

INTRODUCTION

Figure 1A:
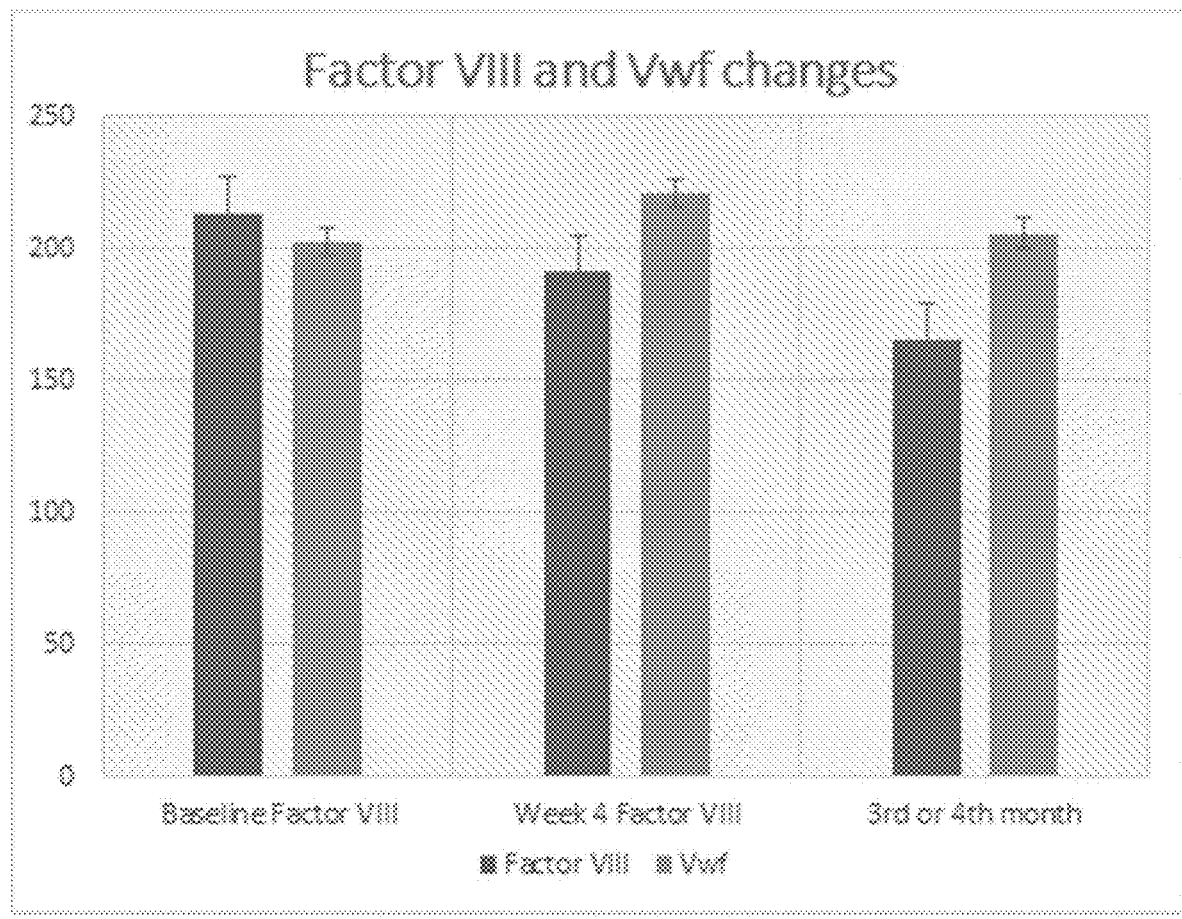
FIG. 1A shows levels of the coagulation factors Factor VIII and von Willebrand's Factor over time in Cushing's syndrome patients treated with relacorilant. (The vertical scale is shown as %; levels of normal subjects would be 100.) Factor VIII (darker column at the left of each pair of columns) and von Willebrand Factor (lighter column at the right of each pair of columns) are shown at baseline, prior to relacorilant administration (left-most pair of columns); after four weeks of relacorilant treatment (middle pair of columns); and after 3 or 4 months of relacorilant treatment (right-most pair of columns). Factor VIII levels are reduced, as compared to baseline, at week four and after 3 or 4 months of relacorilant treatment. Von Willebrand factor levels initially rise somewhat (at four weeks), and then return to baseline levels after 3 or 4 months of relacorilant treatment.

Provided herein are methods for treating a patient at risk for hypercoagulopathy or symptoms and adverse events associated with hypercoagulopathy. In embodiments, the patient at risk for hypercoagulopathy is at risk of developing a deep vein thrombosis (DVT), pulmonary embolism (PE), or a venous thromboembolism (VTE). In embodiments, the patient at risk for hypercoagulopathy suffers from, or is at risk of developing, an inflammatory state. In embodiments, such a patient at risk for hypercoagulopathy; or at risk of developing DVT, PE, or VTE; or suffering from or at risk of developing an inflammatory state, is a patient who suffers from Cushing's syndrome. In embodiments, such a Cushing's syndrome patient may suffer from endogenous Cushing's syndrome, including ACTH-Dependent Cushing's syndrome; the Cushing's syndrome may be pituitary Cushing's syndrome (i.e., Cushing's Disease) and may be ACTH-Independent Cushing's syndrome.

Methods for treating hypercoagulopathy; or DVT, PE, or VTE; or inflammatory states, comprise administration of a glucocorticoid receptor modulator (GRM). In embodiments, the administration of a GRM comprises administration of a glucocorticoid receptor antagonist (GRA). In some embodiments, the GRA is a selective inhibitor of the glucocorticoid receptor. In embodiments, the GRM is a nonsteroidal GRM compound. In embodiments, the GRM is a heteroaryl ketone fused azadecalin GRM (HKGRM). In embodiments, the HKGRM is relacorilant. In embodiments, the GRM is a steroidal compound. In embodiments, the GRM is mifepristone.

In embodiments, Applicant discloses a method of treating hypercoagulopathy in a Cushing's syndrome patient suffering from hypercoagulopathy, the method comprising:
Administering an effective amount of a glucocorticoid receptor modulator (GRM) to said patient, said GRM administration comprising a first anticoagulation therapy,
Whereby said hypercoagulopathy is treated. In embodiments, the first anticoagulation therapy comprises relacorilant administration. In further embodiments, a second anticoagulation therapy is administered to the patient; the second anticoagulation therapy may be administered before, along with, after administration of, or combinations thereof, said first anticoagulation therapy.

In embodiments, Applicant discloses a method of treating hypercoagulopathy in a Cushing's syndrome patient at elevated risk of hypercoagulopathy, the method comprising:
Determining that a Cushing's syndrome patient is at elevated risk of developing hypercoagulopathy,
Administering an effective amount of a glucocorticoid receptor modulator (GRM) to said patient, said GRM administration comprising a first anticoagulation therapy,
Whereby said hypercoagulopathy is treated. In embodiments, the first anticoagulation therapy comprises relacorilant administration. In further embodiments, a second anticoagulation therapy is administered to the patient; the second anticoagulation therapy may be administered before, along with, after administration of, or combinations thereof, said first anticoagulation therapy. In embodiments, said elevated risk is determined by one or more of clotting time (where a short clotting time indicates elevated risk of hypercoagulopathy); levels of blood clotting factors (where elevated levels of clotting factors (e.g., Factor VIII, Factor IX, Factor X, von Willibrand factor, and other clotting factors) indicate elevated risk of hypercoagulopathy); platelet levels (where elevated platelet levels indicate elevated risk of hypercoagulopathy); elevated levels of fibrin, fibronectin, D-dimer, and levels of other fibrin-related molecules indicate elevated risk of hypercoagulopathy; and presence of a blood clot in the patient indicates elevated risk of hypercoagulopathy.

In embodiments of such methods, the patient suffers from Cushing's syndrome, and the method reduced said risk of developing hypercoagulopathy as compared to the risk of developing hypercoagulopathy in a Cushing's syndrome patient who has not received said first anticoagulation therapy. In embodiments, the patient suffers from Cushing's disease. In embodiments, the patient suffers from ACTH-Dependent Cushing's syndrome or ACTH-Independent Cushing's syndrome. In embodiments, the patient suffers from ectopic Cushing's syndrome.

In embodiments of methods of reducing risk of of developing hypercoagulopathy in a Cushing's syndrome patient, the risk of developing hypercoagulopathy is reduced at one month of medical treatment as compared to the risk, one month following surgery, of developing hypercoagulopathy in a Cushing's syndrome patient who has received surgical treatment for Cushing's syndrome.

In embodiments, Applicant discloses a method of reducing risk of developing DVT, PE, or VTE in a patient at risk of developing DVT, PE, or VTE, the method comprising:
Administering an effective amount of a glucocorticoid receptor modulator (GRM) to said Cushing's syndrome patient, said GRM administration comprising a first anticoagulation therapy,
Whereby said risk of developing DVT, PE, or VTE is reduced. In embodiments, the first anticoagulation therapy comprises relacorilant administration. In further embodiments, a second anticoagulation therapy is administered to the patient; the second anticoagulation therapy may be administered before, along with, after administration of, or combinations thereof, said first anticoagulation therapy.

In embodiments of methods of reducing risk of developing DVT, PE, or VTE in a patient at risk of developing DVT, PE, or VTE, the patient suffers from Cushing's syndrome, and said risk of developing DVT, PE, or VTE is reduced as compared to the risk of developing DVT, PE, or VTE in a Cushing's syndrome patient who has not received said first anticoagulation therapy. In embodiments, the patient suffers from Cushing's disease. In embodiments, the patient suffers from ACTH-Dependent Cushing's syndrome or ACTH-Independent Cushing's syndrome. In embodiments, the patient suffers from ectopic Cushing's syndrome.

In embodiments of methods of reducing risk of DVT, PE, or VTE in a patient at risk of developing DVT, PE, or VTE, the risk of developing DVT, PE, or VTE is reduced at one month of medical treatment as compared to the risk, one month following surgery, of developing DVT, PE, or VTE in a Cushing's syndrome patient who has received surgical treatment for Cushing's syndrome.

In embodiments, Applicant discloses a method of method of unmasking and subsequently reducing an inflammatory state in a patient suffering from Cushing's syndrome, the method comprising:

Administering an effective amount of a glucocorticoid receptor modulator (GRM) to said patient, wherein said effective amount of GRM is effective to increase inflammatory symptoms in said patient within about four weeks of beginning said GRM administration, and Is effective to subsequently decrease said inflammatory symptoms in said patient by about three to about four months after beginning said GRM administration, Whereby said inflammatory state in said Cushing's syndrome patient is reduced. In embodiments, the GRM is relacorilant.

In embodiments of methods of unmasking and subsequently reducing an inflammatory state in a patient suffering from Cushing's syndrome, symptoms of said inflammatory state comprise C-reactive protein levels in said Cushing's syndrome patient that are greater than C-reactive protein levels typically found in normal subjects.

In embodiments of the methods disclosed herein, the patient is treated with a GRM (e.g., relacorilant) prior to undergoing surgery for Cushing's syndrome, effective to reduce risk of hypercoagulopathy subsequent to such surgery. It is believed that administration of a GRM (e.g., relacorilant) according to the methods disclosed herein is effective to reduce post-operative risk of hypercoagulopathy, for example, in Cushing's syndrome undergoing surgery. Thus, the methods disclosed herein are believed to provide prophylaxis for hypercoagulopathy in Cushing's syndrome; and, in particular embodiments, the methods disclosed herein are believed to provide prophylaxis for hypercoagulopathy in Cushing's syndrome planning or preparing for surgery; for hypercoagulopathy in Cushing's syndrome undergoing surgery; and for hypercoagulopathy in Cushing's syndrome patients soon after surgery (e.g., within a few days following surgery).

In embodiments of any of the methods disclosed herein, a patient is identified as a patient likely to derive benefit from the methods of treatment by being identified as having short blood coagulation time, excessive levels of blood coagulation factors (e.g., von Willebrand factor, Factor VIII, abnormal platelet levels, or other indication of abnormal blood coagulation indicative of increased risk of a coagulation disorder).

In embodiments of the methods disclosed herein, the GRM is a GRA. In embodiments, the GRM is a heteroaryl ketone fused azadecalin GRM compound (HKGRM). In embodiments, the HKGRM is relacorilant. In embodiments, the GRM is mifepristone.

In embodiments, the GRM is administered orally to the patient. In embodiments, the GRM is administered once per day. In embodiments, the GRM is administered twice per day. In embodiments, the GRM is administered three times per day. In embodiments, the GRM is administered once every other day. In embodiments, the GRM is administered once every third day.

HKGRM compounds suitable for use in the methods disclosed herein include, without limitation:

(R)-(1-(4-fluorophenyl)-6-((1-methyl-1H-pyrazol-4-yl) sulfonyl)-4,4a,5,6,7,8-hexahydro-1H-pyrazolo[3,4-g]iso-quinolin-4a-yl)(4-(trifluoromethyl)pyridin-2-yl)methanone (termed "relacorilant"; also termed "CORT125134"), which has the following structure:

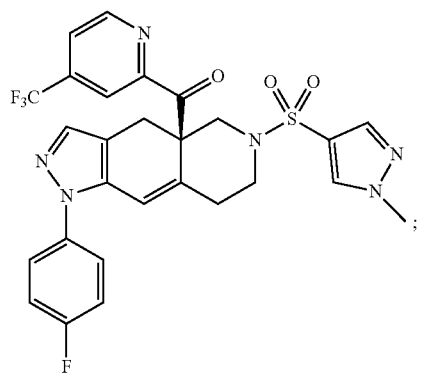 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

(R)-(1-(4-fluorophenyl)-6-((4-(trifluoromethyl)phenyl) sulfonyl)-4,4a,5,6,-7,8-hexahydro-1H-pyrazolo[3,4-g] isoquinolin-4a-yl)(thiazol-2-yl)methanone (termed "CORT122928"), which has the following structure:

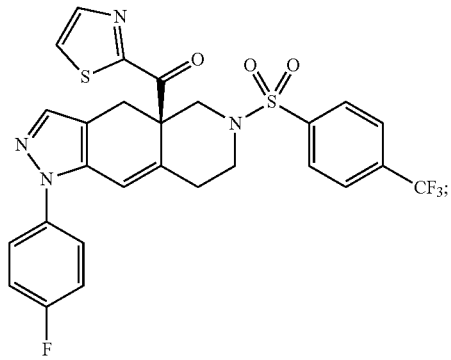 [SMILES: O=C(c1nccs1)[C@]12Cc3cnn(-c4ccc(F)cc4)c3C=C1CCN(S(=O)(=O)c1ccc(C(F)(F)F)cc1)C2]

and (R)-(1-(4-fluorophenyl)-6-((4-(trifluoromethyl)phenyl) sulfonyl)-4, 4a, 5,6,7,8-hexahydro-1-H-pyrazolo P,4-g] isoquinolin-4a-yl) (pyridin-2-yl)methanone (termed "CORT113176"), which has the following structure:

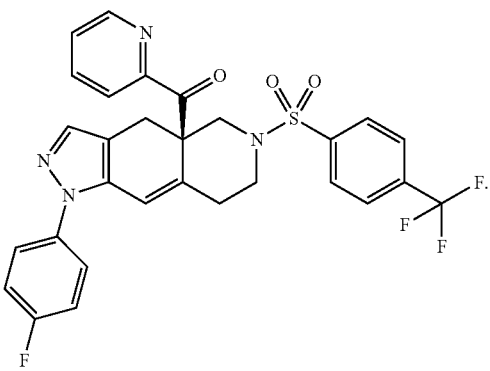 [SMILES: O=C(c1ccccn1)[C@]12Cc3cnn(-c4ccc(F)cc4)c3C=C1CCN(S(=O)(=O)c1ccc(C(F)(F)F)cc1)C2]

In embodiments, the GRM is a heteroaryl ketone fused azadecalin compound selected from relacorilant, CORT122928, and CORT113176. In embodiments, the dose of HKGRM is administered orally to the patient. In embodiments, the dose of HKGRM is selected from 50 milligrams (mg), 100 mg, 150 mg, 200 mg, 250 mg, 300 mg, 350 mg, 400 mg, 450 mg, 500 mg, 550 mg, 600 mg, 650 mg, and 700 mg. In embodiments, the HKGRM dose is a daily dose. In embodiments, the HKGRM dose is administered once per day. In embodiments, the HKGRM is relacorilant.

In embodiments, the GRM is a steroidal compound. In embodiments, the GRM is a glucocorticoid receptor antagonist (GRA). In embodiments, the GRM is mifepristone. In embodiments, the dose of mifepristone is administered orally to the patient. In embodiments, the dose of mifepristone is selected from 300 milligrams (mg), 600 mg, 900 mg, and 1200 mg. In embodiments, the dose of mifepristone is a daily dose. In embodiments, the dose of mifepristone is administered once per day.

In embodiments, the patient is administered a second anticoagulation therapy in addition to the GRM anticoagulation therapy. In embodiments, the second anticoagulation therapy may include, for example, administration of a thrombolytic agent, administration of an anticoagulant, administration of an anti-platelet agent (an agent that inhibits platelet aggregation), or other agent. In embodiments, the second anticoagulation therapy comprises administration of a thrombolytic agent selected from tissue plasminogen activator (tPA), streptokinase, and urokinase. In embodiments, the second anticoagulation therapy comprises administration of an anti-platelet agent selected from aspirin, clopidogrel, dipyridamole, and abciximab. In embodiments, the second anticoagulation therapy comprises administration of a heparin, including low-molecular weight heparin. In embodiments, the second anticoagulation therapy comprises administration of an agent selected from heparin, warfarin (coumadin), Fondaparinux (Arixtra), rivaroxaban (Xarelto), dabigatran (Pradaxa), apixaban (Eliquis), edoxaban (Savaysa), and enoxaparin (Lovenox). In embodiments, the second anticoagulation therapy is administered at the same time, or closely in time, to the administration of the GRM anticoagulation therapy. In embodiments, the second anticoagulation therapy is administered at a time after the administration of the GRM anticoagulation therapy. In embodiments, the time after said administration of the GRM anticoagulation therapy is a time selected from one hour, two hours, three hours, four hours, five hours, ten hours, twelve hours, one day, two days, three days, one week, and two weeks. In embodiments, the second anticoagulation therapy is administered at a time before the administration of the GRM anticoagulation therapy. In embodiments, the time before said administration of the GRM anticoagulation therapy is a time selected from one hour, two hours, three hours, four hours, five hours, ten hours, twelve hours, one day, two days, three days, one week, and two weeks.

In embodiments, the methods disclosed herein may be directed to the treatment of a patient not otherwise in need of treatment with a GRM or a GRA. Such a patient "not otherwise in need of treatment with a GRM or a GRA" is a patient not suffering from a condition known in the art to be effectively treatable with a GRM or a GRA. Conditions known in the art to be effectively treatable with a GRM or GRA can include, but are not limited to: drug withdrawal, psychosis, dementia, stress disorders, and psychotic major depression. Thus, in embodiments, the present methods are directed to patients not otherwise in need of, or not receiving, treatment with a GRM or a GRA.

Applicant discloses herein that relacorilant treatment is at least as effective as surgery (to remove a tumor or tumors causing excess cortisol levels) in terms of the improvement in hypercoagulopathy in Cushing's syndrome patients. A study of changes in Factor VIII levels in Cushing's patients treated with surgery determined that Factor VIII levels initially rose following surgery, showing worsening levels of Factor VIII at one month following surgical treatment (Casonato, et al. Blood Coagulation and Fibrinolysis 10(3):145-151 (1999)). As shown in FIG. 1, Factor VIII levels in Cushing's syndrome patients treated with relacorilant showed a gradual decline to normal range of Factor VIII levels without surgery. These results show more favorable changes in factor VIII levels with medical treatment (relacorilant administration) as compared to changes in factor VIII levels following surgery (worsening levels at one month following surgical treatment). Thus, the coagulation profile observed in Cushing's syndrome patients treated with relacorilant was better than the coagulation profile observed in Cushing's syndrome patients treated with surgery. Relacorilant also has the advantage of not raising cortisol and not increasing the risk of hypokalemia (see U.S. Patent Application 62/783,015, filed Dec. 20, 2018, hereby incorporated by reference in its entirety).

The DVT, PE, and VTE outcomes observed in Cushing's syndrome patients treated with relacorilant as compared to DVT, PE, and VTE outcomes observed in Cushing's syndrome patients treated with surgery are consistent with the results shown in FIG. 1 for coagulation factors. No thromboembolic events were observed in the clinical study of 35 Cushing's syndrome patients treated with relacorilant, while in the published surgical series the VTE rates were high in patients not treated with anti-coagulants.

As noted above, factor VIII levels improved at week 4 and normalized at the end of the study ($3^{rd}$ or $4^{th}$ month) in patients treated with relacorilant. Applicant notes that the changes observed in the levels of von Willebrand factor observed in Cushing's syndrome patients treated with relacorilant (see FIG. 1) were similar to those that have been observed in Cushing's syndrome patients treated with surgery. Thus, Von Willebrand factor levels followed the same trend as was observed in patients with successful surgery: Von Willebrand factor levels increased immediately following surgery, and started coming down 3 months after surgery.

Without being bound by theory, Applicant notes that Von Willebrand factor is elevated in patients with inflammatory conditions, and further notes that glucocorticoids decrease Von Willebrand factor levels. The temporal trend of C-Reactive Protein (an inflammation marker) is similar to that of Von Willebrand factor levels in Cushing's patients treated with relacorilant. Thus, it appears that GRM treatment unmasks an underlying inflammatory state; such an underlying inflammatory state was chronically suppressed by the cortisol excess in Cushing's syndrome patients. GRM (e.g., relacorilant) treatment relieves the effects of such cortisol excess, thereby unmasking the underlying inflammatory state, and then, over time, reducing that inflammation (seen by the subsequent decrease in C-Reactive Protein by the $3^{rd}$ or $4^{th}$ month after beginning GRM treatment). Thus, the changes in C-Reactive Protein levels correlate closely with the changes we observed in von Willebrand Factor levels. In addition, these changes provide further additional pharmacodynamic evidence of the GR antagonistic effects of relacorilant treatment.

I. Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "pituitary tumor" as used herein includes, but is not limited to, lactotrophic adenoma or prolactinoma, ACTH-secreting adenoma, somatotrophic adenomas, corticotrophic adenoma, gonadotrophic adenoma, thyrotrophic adenomas, and null cell adenoma. An ACTH-secreting pituitary tumor may be found in the anterior lobe of the pituitary, usually measuring less than about 5 mm in diameter. Most pituitary ACTH-secreting adenomas (about 90%) are small in size (i.e., microadenomas).

The term "Cushing's syndrome" refers to a disease caused by prolonged exposure to endogenous or exogenous glucocorticoids. Cushing's syndrome patients often suffer hyperglycemia secondary to hypercortisolism. Symptoms of Cushing's syndrome include, but are not limited to one or more of the following: hyperglycemia, high blood pressure, weight gain, poor short term memory, poor concentration, irritability, excess hair growth, impaired immunological function, ruddy complexion, extra fat in the neck region, moon face, fatigue, red stretch marks, irregular menstruation, or a combination thereof. Symptoms of Cushing's syndrome can additionally or alternatively include without limitation one or more of the following: insomnia, recurrent infection, thin skin, easy bruising, weak bones, acne, balding, depression, hip or shoulder weakness, swelling of the extremities, diabetes mellitus, elevated white blood cell count, hypokalemic metabolic alkalosis, or a combination thereof.

The term "endogenous Cushing's syndrome" refers to a type of Cushing's syndrome caused by endogenous overproduction of cortisol by the patient, typically due to a pituitary ACTH-secreting tumor (Cushing's disease), a non-pituitary ACTH-secreting tumor, or a cortisol-secreting tumor (adrenal or extra-adrenal). ACTH-secreting tumors can be, e.g., pituitary adenomas, pituitary adenocarcinomas, carincinoid tumors, neuroendocrine tumors, or other tumors. Cortisol-secreting tumors include, and are not limited to, cortisol producing adrenal adenomas, adrenocortical carcinomas, primary pigmented micronodular adrenal disease (PPNAD), ACTH independent macronodular adrenal hyperplasia (AIMAH), and extra-adrenal cortisol secreting tumors, e.g., ovarian carcinomas.

"Patient" and "subject" are used interchangeably to refer to a human subject who may be in need of treatment for Cushing's syndrome. In some cases, the patient may be in need of treatment for Cushing's Disease.

The term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, epicutaneous, subcutaneous, intraperitoneal, intraventricular, and intracranial. Other modes of delivery include, but are not limited to, the use of liposomal formulations, intravenous infusion, transdermal patches, etc.

The term "sample" refers to a biological sample obtained from a human subject. Such samples are typically removed from the subject, and, when obtained, become entirely separate from the subject (i.e., are in vitro samples). The sample can be any cell, tissue or fluid sample obtained from a human subject. The sample may be, e.g., a blood sample, a saliva sample, a urine sample, or other sample obtained from the patient. Samples can be subject to various treatment, storage or processing procedures before being analyzed according to the methods described herein. Generally, the terms "sample" or "samples" are not intended to be limited by their source, origin, manner of procurement, treatment, processing, storage or analysis, or any modification. Thus, in embodiments, samples are in vitro samples and may be analyzed using in vitro methods. The methods disclosed herein are in vitro methods when used with samples obtained from, and removed from, the human subject.

The term "adrenocorticotropic hormone" or "ACTH" refers to a polypeptide-based hormone that is normally produced and secreted by the anterior pituitary gland. ACTH stimulates secretion of cortisol and other glucocorticoids (GCs) by specialized cells of the adrenal cortex. In healthy mammals, ACTH secretion is tightly regulated. ACTH secretion is positively regulated by corticotropin releasing hormone (CRH), which is released by the hypothalamus. ACTH secretion is negatively regulated by cortisol and other glucocorticoids. A disruption to the tightly regulated hypothalamus-pituitary-adrenal gland (HPA) axis can cause low levels of ACTH and cortisol, and in turn, secondary adrenal insufficiency.

The term "glucocorticoid" ("GC") includes any compound known in the art that is referred to as a glucocorticoid receptor agonist, glucocorticoid, glucocorticosteroid, corticoid, corticosteroid, or steroid that binds to and activates a glucocorticoid receptor. "Glucocorticosteroid" refers to a steroid hormone or steroidal molecule that binds to the glucocorticoid receptor. Glucocorticosteroids are GCs. Glucocorticosteroids are typically characterized by having 21 carbon atoms, an $\alpha,\beta$-unsaturated ketone in ring A, and an $\alpha$-ketol group attached to ring D. They differ in the extent of oxygenation or hydroxylation at C-11, C-17 and C-19 (Rawn, "Biosynthesis and Transport of Membrane Lipids and Formation of Cholesterol Derivatives," in Biochemistry, Daisy et al. (eds.), 1989, pg. 567).

As used herein, the term "cortisol" refers to the naturally occurring glucocorticoid hormone (also known as hydrocortisone) having the structure:

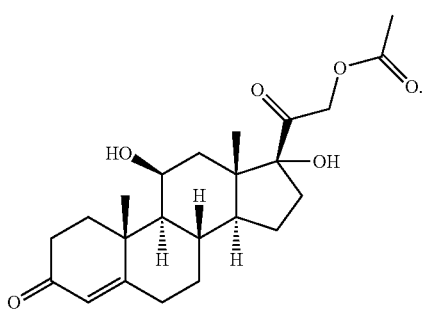

Cortisol is a glucocorticoid hormone that is produced by the zona fasciculata of the adrenal gland. The term "total cortisol" refers to cortisol that is bound to cortisol-binding globulin (CBG or transcortin) and free cortisol (cortisol that is not bound to CBG). The term "free cortisol" refers to cortisol that is not bound to cortisol-binding globulin (CBG or transcortin). As used herein, the term "cortisol" refers to total cortisol, free cortisol, and/or cortisol bound to CBG.

"Glucocorticoid receptor" ("GR") refers to the type II GR which specifically binds to cortisol and/or cortisol analogs such as dexamethasone (See, e.g., Turner & Muller, *J Mol Endocrinol*, 2005 35 283-292). The GR is also referred to as the cortisol receptor. The term includes isoforms of GR, recombinant GR and mutated GR. Inhibition constants ($K_i$) against the human GR receptor type II (Genbank: P04150) are between 0.0001 nM to 1,000 nM; preferably between 0.0005 nM to 10 nM, and most preferably between 0.001 nM to 1 nM.

The term "glucocorticoid receptor modulator" or "GRM" refers to any composition or compound which changes ("modulates") the binding of a glucocorticoid receptor (GR) agonist, such as cortisol, or cortisol analogs, synthetic or natural, to a GR, or which changes ("modulates") the activity of a GR resulting from GR agonist binding. Thus, a GRM alters the effect of GR agonist binding that would occur in the absence of the GRM.

The term "glucocorticoid receptor antagonist" or "GRA" refers to a GRM which partially or completely inhibits (antagonizes) the binding of a glucocorticoid receptor (GR) agonist, such as cortisol, or cortisol analogs, synthetic or natural, to a GR. A GRA is a GRM which provides antagonistic modulation of the effect of GR agonist binding that would occur in the absence of the GRA. A "specific glucocorticoid receptor antagonist" refers to any composition or compound which inhibits any biological response associated with the binding of a GR to an agonist. By "specific," the drug preferentially binds to the GR rather than other nuclear receptors, such as mineralocorticoid receptor (MR), androgen receptor (AR), or progesterone receptor (PR). It is preferred that the specific glucocorticoid receptor antagonist bind GR with an affinity that is 10× greater ($\frac{1}{10}^{th}$ the $K_d$ value) than its affinity to the MR, AR, or PR, both the MR and PR, both the MR and AR, both the AR and PR, or to the MR, AR, and PR. In a more preferred embodiment, the specific glucocorticoid receptor antagonist binds GR with an affinity that is 100× greater ($\frac{1}{100}^{th}$ the $K_d$ value) than its affinity to the MR, AR, or PR, both the MR and PR, both the MR and AR, both the AR and PR, or to the MR, AR, and PR.

The term "selective inhibitor" in the context of glucocorticoid receptor, refers to a chemical compound that selectively interferes with the binding of a specific glucocorticoid receptor agonist and the glucocorticoid receptor.

The term "steroidal backbone" in the context of glucocorticoid receptor antagonists containing such refers to glucocorticoid receptor antagonists that contain modifications of the basic structure of cortisol, an endogenous steroidal glucocorticoid receptor ligand. The basic structure of a steroidal backbone is provided as Formula I:

Formula I

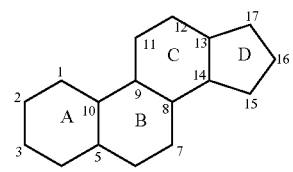

Steroidal Backbone

The two most commonly known classes of structural modifications of the cortisol steroid backbone to create glucocorticoid antagonists include modifications of the 11-β hydroxy group and modification of the 17-β side chain (See, e. g., Lefebvre (1989) J. Steroid Biochem. 33: 557-563).

As used herein, the term "mifepristone" refers to 11β-(4-dimethylaminophenyl)-17β-hydroxy-17α-(1-propynyl)-estra-4,9-dien-3-one), also referred to as RU486, or as RU38.486, or as 17-beta-hydroxy-11-beta-(4-dimethyl-aminophenyl)-17-alpha-(1-propynyl)-estra-4,9-dien-3-one). Mifepristone binds to the glucocorticoid receptor (GR), typically with high affinity, and inhibits the biological effects initiated/mediated by the binding of any cortisol or cortisol analogue to a GR receptor. Salts, hydrates and prodrugs of mifepristone are all included in the term "mifepristone" as used herein. Thus, used herein, "mifepristone" refers to the molecule that has the following structure:

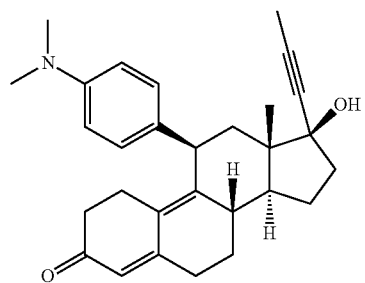

and to salts, hydrates and prodrugs thereof, and pharmaceutical compositions thereof.

As used herein, the phrase "non-steroidal backbone" in the context of glucocorticoid receptor antagonists containing such refers to glucocorticoid receptor antagonists that do not share structural homology to, or are not modifications of, cortisol. Such compounds include synthetic mimetics and analogs of proteins, including partially peptidic, pseudopeptidic and non-peptidic molecular entities.

Non-steroidal GRM compounds also include glucocorticoid receptor antagonists having a heteroaryl ketone fused azadecalin backbone. Exemplary GRMs having a heteroaryl ketone fused azadecalin backbone include those described in U.S. Pat. Nos. 8,859,774; 9,273,047; and 9,707,223. All patents, patent publications, and published articles cited herein, both supra and infra, are hereby incorporated by reference in their entireties, including all compounds and compositions disclosed in the patents, patent publications, and published articles cited herein.

As used herein, the term "relacorilant" refers to the heteroaryl ketone fused azadecalin compound (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (Example 18 of U.S. Pat. No. 8,859,774), which has the following structure:

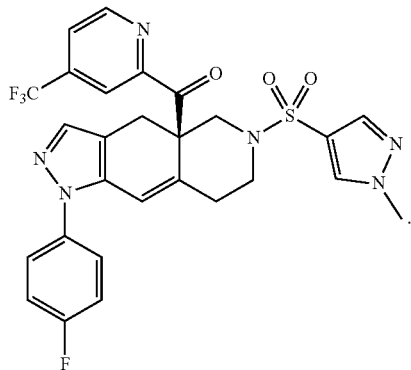 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

As used herein, the term "CORT122928" refers to the heteroaryl ketone fused azadecalin compound (R)-(1-(4-fluorophenyl)-6-((4-(trifluoromethyl)phenyl)sulfonyl)-4,4a,5,6,-7,8-hexahydro-1H-pyrazolo[3,4-g]isoquinolin-4a-yl)(thiazol-2-yl)methanone (Example 1C of U.S. Pat. No. 8,859,774), which has the following structure:

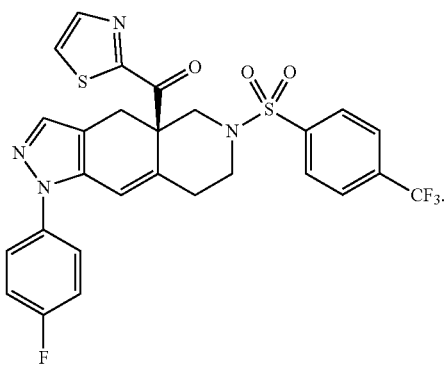 [SMILES: O=C(c1nccs1)[C@]12Cc3cnn(-c4ccc(F)cc4)c3C=C1CCN(S(=O)(=O)c1ccc(C(F)(F)F)cc1)C2]

As used herein, the term "CORT113176" refers to the heteroaryl ketone fused azadecalin compound (R)-(1-(4-fluorophenyl)-6-((4-(trifluoromethyl)phenyl) sulfonyl)-4,4a, 5,6,7,8-hexahydro-1-H-pyrazolo P,4-g]isoquinolin-4a-yl) (pyridin-2-yl)methanone (Example 1 of U.S. Pat. No. 8,859,774) which has the following structure:

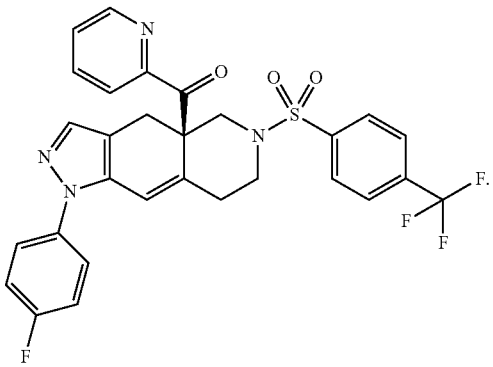 [SMILES: O=C(c1ccccn1)[C@]12Cc3cnn(-c4ccc(F)cc4)c3C=C1CCN(S(=O)(=O)c1ccc(C(F)(F)F)cc1)C2]

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

Methods of Diagnosis and Treatment

Cushing's syndrome may be diagnosed without knowledge of the source of the excess cortisol or GC action which characterizes the syndrome. Thus, while treatment (e.g., administration of a GRM such as mifepristone) may begin, further diagnostic information may need to be acquired in order to provide the patient with the best treatment for their condition. The present methods provide GRM treatment of Cushing's syndrome and at the same time that treatment is effective to treat conditions associated with Cushing's syndrome, such as hypercoagulopathy; DVT, PE, and VTE; and inflammatory states in the patient.

The methods may include obtaining biological samples from a patient suffering from Cushing's syndrome. The biological sample can be saliva, urine, whole blood, plasma, serum, or another biological sample from the patient. In some embodiments, the biological sample is a blood sample. In embodiments, detection or measurements of factors of the intrinsic pathway of blood clotting are performed using such a sample; in embodiments, detection or measurements of factors of the extrinsic pathway (also termed the tissue factor pathway) of blood clotting are performed using such a sample. In embodiments, coagulation parameters (such as, e.g., clotting time), or platelets, or levels of coagulation factors (such as, e.g., Factor VIII, von Willebrand's factor, factor IX, factor X, factor XI, factor XII (Hageman factor), factor XIII, fibrin, fibrinogen, thrombin, prothrombin, plasma thromblastin antecedent, Stuart factor, etc.) are determined from a blood sample obtained from the patient. In embodiments, markers or factors indicative of inflammation and of the presence, extent, or absence of an inflammatory state in the patient (such as, e.g., erythrocyte sedimentation rate, and levels of C-Reactive Protein, procalcitonin, eosinophil counts, platelet counts, cytokine levels (e.g., levels of interleukin-6, tumor necrosis factor, adiponectin, monocyte chemoattractant protein 1 (MCP-1), CD40 ligand, lipoprotein-associated phospholipase A(2)

(Lp-PLA(2)), fibrinogen, ferritin, etc.) are determined from a blood sample obtained from the patient.

Normal ranges of some of such coagulation factors and inflammation markers include: APTT: 22-34 seconds; von Willibrand Factor: 50-217%; Factor VIII: 50-180%; Factor IX: 60-160%; Factor X: 70-150%; D-Dimer: less than or equal to 0.4999 µg/mL; plasma fibrinogen: 2-4 g/L; thrombin-antithrombin: less than or equal to 3.99 µg/L; osteocalcin: 8-37 UG/L; C-reactive Protein: less than or equal to 3.099 µg/L; platelet count: 130,000-400,000 cells per cubic millimeter; eosinophils: 0.05-0.55 thousands per µL (or, as percent—eosinophils: 0-7% of white blood cells).

Hypercoagulopathy may be diagnosed by blood test, including measurement of blood clotting time, fibrin degradation products (e.g., d-dimer test), erythrocyte sedimentation rate (or other blood viscosity test), and clotting parameters (e.g., measuring platelets, measuring APTT (activated prothrombin time, also known as activated partial thromboplastin time (aPTT)), or by other suitable test); by physical examination of the patient to detect a blood clot, by imaging (e.g., ultrasound or other suitable imaging) to detect a blood clot, or by other means. Coagulation markers which may be measured and tracked using blood tests include, for example, Factor VIII, von Willebrand Factor, platelet counts, activated partial thromboplastin time (aPTT), Factor V, Factor X, thrombin-antithrombin, and other factors. Blood clotting time may be measured by, e.g., APTT or other test.

Deep vein thrombosis (DVT), pulmonary embolism (PE), Venous Thromboembolism (VTE), and other such thrombotic disorders may be diagnosed by physical examination of the patient; by blood test (e.g., d-dimer test for the presence of fibrin degradation products, or by other suitable test), platelet counts and other blood tests; by imaging (e.g., ultrasound CT scan, MRI, or other suitable imaging); or by other suitable means.

The presence of an inflammatory state may be diagnosed by physical examination of the patient; observation of accumulation of monocytes, mast cells, T-cells, or other blood cells; by blood test for levels of inflammatory factors, such as, e.g., cytokines, chemokines, interleukins, histamine, prostaglandins, C-reactive protein, tumor necrosis factor, and others.

Glucocorticoid Receptor Antagonists

The methods of the present invention generally provide administering a glucocorticoid receptor modulator (GRM), which may be a glucocorticoid receptor antagonist (GRA). In some cases, the GRM is a specific GRM. As used herein, a specific GRM refers to a composition or compound which modulates any biological response associated with the binding of a glucocorticoid receptor (GR) to an agonist by preferentially binding to the GR rather than another nuclear receptor (NR). In some cases, the GRA is a specific GRA. As used herein, a specific GRA refers to a composition or compound which inhibits any biological response associated with the binding of a GR to an agonist by preferentially binding to the GR rather than another nuclear receptor (NR). In some embodiments, the specific GRM binds preferentially to GR rather than the mineralocorticoid receptor (MR), androgen receptor (AR), or progesterone receptor (PR). In an exemplary embodiment, the specific GRM binds preferentially to glucocorticoid receptor rather than the mineralocorticoid receptor (MR). In another exemplary embodiment, the specific GRM binds preferentially to GR rather than the progesterone receptor (PR). In another exemplary embodiment, the specific GRM binds preferentially to glucocorticoid receptor rather than the androgen receptor (AR). In yet another exemplary embodiment, the specific GRM binds preferentially to glucocorticoid receptor in comparison to MR and PR, MR and AR, PR and AR, or MR, PR, and AR.

Synthetic 11-beta phenyl-aminodimethyl steroids include mifepristone, also known as RU486, or 17-β-hydrox-11-β-(4-dimethyl-aminophenyl) 17-α-(1-propynyl)estra-4,9-dien-3-one). Mifepristone has been shown to be a powerful antagonist of both the progesterone and glucocorticoid (GR) receptors. Thus, in some embodiments, the GRM is mifepristone. Such treatments may be useful in treating hypercoagulopathy, VTE, and inflammatory states associated with Cushing's syndrome.

Non-Steroidal Anti-Glucocorticoids as Glucocorticoid Receptor Modulators

Non-steroidal GRMs are also used in the methods of the invention to treat hypercoagulopathy, VTE, and inflammatory states in a subject. In some embodiments, hypercoagulopathy, VTE, and inflammatory states may be treated with an effective amount of a non-steroidal GRM having a heteroaryl ketone fused azadecalin backbone. For example, hypercoagulopathy, VTE, and inflammatory states can be treated with effective amounts of one of the foregoing GRMs. Exemplary GRMs having a heteroaryl ketone fused azadecalin backbone include those described in U.S. Pat. No. 8,859,774.

Pharmaceutical Compositions of Glucocorticoid Receptor Modulators

The GRM administered in the practice of the methods disclosed herein can be prepared in any suitable form, including in a wide variety of oral, parenteral and topical dosage forms. Oral preparations of either include tablets, pills, powder, dragees, capsules, liquids, lozenges, cachets, gels, syrups, slurries, suspensions, etc., suitable for ingestion by the patient. The GRA compositions of the present invention can also be administered by injection, that is, intravenously, intramuscularly, intracutaneously, subcutaneously, intraduodenally, or intraperitoneally. Also, the GRM compositions described herein can be administered by inhalation, for example, intranasally. Additionally, the GRM compositions of the present invention can be administered transdermally. The GRM compositions of this invention can also be administered by intraocular, intravaginal, and intrarectal routes including suppositories, insufflation, powders and aerosol formulations (for examples of steroid inhalants, see Rohatgi, J. Clin. Pharmacol. 35:1187-1193, 1995; Tjwa, Ann. Allergy Asthma Immunol. 75:107-111, 1995). Accordingly, the present invention provides pharmaceutical compositions of a GRM including a pharmaceutically acceptable carrier or excipient and a GRM compound as disclosed herein.

For preparing pharmaceutical compositions from the GRM compound as disclosed herein, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving one or more compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compounds of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The GRM compositions provided herein can also be delivered as microspheres for slow release in the body. For example, microspheres can be formulated for administration via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In another embodiment, the GRM compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These GRM formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the GRM formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, J. *Microencapsul.* 13:293-306, 1996; Chonn, *Curr. Opin. Biotechnol.* 6:698-708, 1995; Ostro, *Am. J. Hosp. Pharm.* 46:1576-1587, 1989).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

The GRM composition can also contain other compatible therapeutic agents. The compounds described herein can be used in combination with one another, with other active agents known to be useful in antagonizing a glucocorticoid receptor, or with adjunctive agents that may not be effective alone, but may contribute to the efficacy of the active agent.
Administration of a Glucocorticoid Receptor Modulator The GRM may be a GRA, which can be a selective inhibitor of the glucocorticoid receptor. The GRM may have a steroidal backbone, and may be, e.g., mifepristone. The GRM may have a non-steroidal backbone. In some cases, the backbone of the GRM is a heteroaryl ketone fused azadecalin. Additional details of GRM that can be used in the method provided herein are described below. The GRM may be administered once, or twice, or more times during a day. The GRM may be administered for one day; for two days; for three days; or for more days.

The GRM compounds or compositions useful in the methods disclosed herein can be delivered by any suitable means, including oral, parenteral (e.g., intravenous injection or intramuscular injection) and topical methods. Transdermal administration methods, by a topical route, can be formulated as applicator sticks, solutions, suspensions, emulsions, gels, creams, ointments, pastes, jellies, paints, powders, and aerosols.

The GRM dose may be administered at any time during the day or night. In embodiments of the methods provided herein, a GRM is administered in the morning; and may be administered in the morning prior to the morning meal ("fasted" administration) or may be administered in the morning within about 30 minutes or within about one hour after the patient begins eating the morning meal ("fed" administration). In some embodiments of the methods provided herein, at least one dose of a GRM is administered at about 11 P.M. (e.g., 2300 h) and the level of total or free cortisol (e.g., morning plasma total cortisol, morning serum total cortisol, morning salivary cortisol, serum free cortisol, plasma free cortisol, or urine free cortisol) is measured the following morning at about 8 a.m. or no later than 10 hours after GRM administration.

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

GRMs can be administered orally. For example, the GRM can be administered as a pill, a capsule, or liquid formulation as described herein. Alternatively, GRMs can be provided via parenteral administration. For example, the GRM can be administered intravenously (e.g., by injection or infusion). Additional methods of administration of the compounds described herein, and pharmaceutical compositions or formulations thereof, are described herein.

In some embodiments, the GRM is administered in one dose. In other embodiments, the GRM is administered in more than one dose, e.g., 2 doses, 3 doses, 4 doses, 5 doses, 6 doses, 7 doses, or more. In some cases, the doses are of an equivalent amount. In other cases, the doses are of different amounts. The doses can increase or taper over the duration of administration. The amount will vary according to, for example, the GRM properties and patient characteristics.

Any suitable GRM dose may be used in the methods disclosed herein. The dose of GRM that is administered can be at least about 50 milligrams (mg) per day, about 100 mg/day, about 150 mg/day, about 200 mg/day, about 250 mg/day, about 300 mg/day, about 350 mg/day, about 400 mg/day, about 450 mg/day, about 500 mg/day, about 550 mg/day, about 600 mg/day, or more. For example, where the GRA is the HKGRM relacorilant, the HKGRM dose may be, e.g., 50 milligrams (mg) per day, 100 mg/day, 150 mg/day, 200 mg/day, 250 mg/day, 300 mg/day, 350 mg/day, 400 mg/day, 450 mg/day, 500 mg/day, 550 mg/day, or 600 mg/day. For example, where the GRA is mifepristone, the GRM dose may be, e.g., 300 mg/day, or 600 mg/day, or 900 mg/day, or 1200 mg/day of mifepristone. In embodiments, the GRM is administered orally. In some embodiments, the GRM is administered in at least one dose. In other words, the GRM can be administered in 1, 2, 3, 4, 5, 6, 7, 8, 9, 10 or more doses. In embodiments, the GRM is administered orally in 1, 2, 3, 4, 5, 6, 7, 8, 9, 10 or more doses.

The patient may be administered at least one dose of GRM in one or more doses over, for example, a 2-48 hour period. The GRM may be administered orally. The patient may be administered daily doses of GRM for one week, or two weeks, or three weeks, or four weeks, or two months, for three months, or four months, or five months, or six months, or nine months, or one year, or one and one half years, or two years, or more. In some embodiments, the GRM is administered as a single dose. In some embodiments, the GRM is administered as a single daily dose. In other embodiments, the GRM is administered in more than one dose, e.g. 2 doses, 3 doses, 4 doses, 5 doses, or more doses per day. In some embodiments, the GRM is administered over 2-48 hours, 2-36 hours, 2-24 hours, 2-12 hours, 2-8 hours, 8-12 hours, 8-24 hours, 8-36 hours, 8-48 hours, 9-36 hours, 9-24 hours, 9-20 hours, 9-12 hours, 12-48 hours, 12-36 hours, 12-24 hours, 18-48 hours, 18-36 hours, 18-24 hours, 24-36 hours, 24-48 hours, 36-48 hours, or 42-48 hours.

EXAMPLES

The following examples are offered to illustrate, but not to limit, the claimed invention.

Treatment with relacorilant led to improvement in hyperglycemia and hypertension, generally observed within two weeks of achieving a therapeutic dose of relacorilant. In addition, significant improvements were also observed in a number of other cortisol-related comorbidities as seen in TABLE 1 below:

TABLE 1

Relacorilant Treatment Leads to Improvements in Cushing's syndrome Patients

| Endpoint | Units | Mean Change from Baseline | P-value |
| --- | --- | --- | --- |
| Coagulopathy (Factor VIII) | % | −18.94 | <0.03 |
| Coagulopathy (Platelets) | $10^9$/L | −68.82 | <0.0001 |
| Coagulopathy (APTT) | Seconds | +1.45 | <0.05 |
| Inflammation (eosinophils) | $10^9$/L | 0.05 | <0.01 |
| Serum Osteocalcin | µg/L | 3.00 | <0.01 |

In TABLE 1 above, the P-value is a Wilcoxon Signed Rank P-value; mean change from baseline indicates the mean change from the initial (baseline) values to the last-observed values; Factor VIII values are reported as percent of normal values; platelet counts and eosinophil counts are reported as numbers of cells per liter; APTT indicates activated partial thromboplastin time, measured in seconds; and serum osteocalcin measures levels of the vitamin K-related hormone osteocalcin outside of bone.

FIG. 1A shows levels of the coagulation factors over time in Cushing's syndrome patients treated with relacorilant. Relacorilant was administered to the patients once per day for four months. Two groups of Cushing's syndrome patients received relacorilant. Group 1 received 100 milligrams per day (mg/day) which, if tolerated, was raised to 200 mg/day for the 16 weeks of the study. Group 2 received relacorilant doses according to the following schedule: the starting doses were 250 milligrams (mg) per day of relacorilant for four weeks, followed by 300 mg/day relacorilant for the next four weeks, followed by 350 mg/day relacorilant for a further four weeks, and then 400 mg relacorilant for another four weeks. (Some patients did not tolerate the higher doses, and remained on a lower dose for the duration of the study, or ended the study prior to 16 weeks.)

In FIG. 1A, normalized levels of Factor VIII (darker column at the left of each pair of columns) and von Willebrand Factor (lighter column at the right of each pair of columns (Vwf)) are shown (as % of the levels found in normal subjects). Factor VIII and von Willebrand Factor at baseline, prior to relacorilant administration (left-most pair of columns); after four weeks of relacorilant treatment (middle pair of columns); and after 3 or 4 months of relacorilant treatment (right-most pair of columns). Factor VIII levels are reduced, as compared to baseline, at week four and after 3 or 4 months of relacorilant treatment. Von Willebrand factor levels initially rise somewhat (at four weeks), and then return to baseline levels after 3 or 4 months of relacorilant treatment.

Figure 2A:
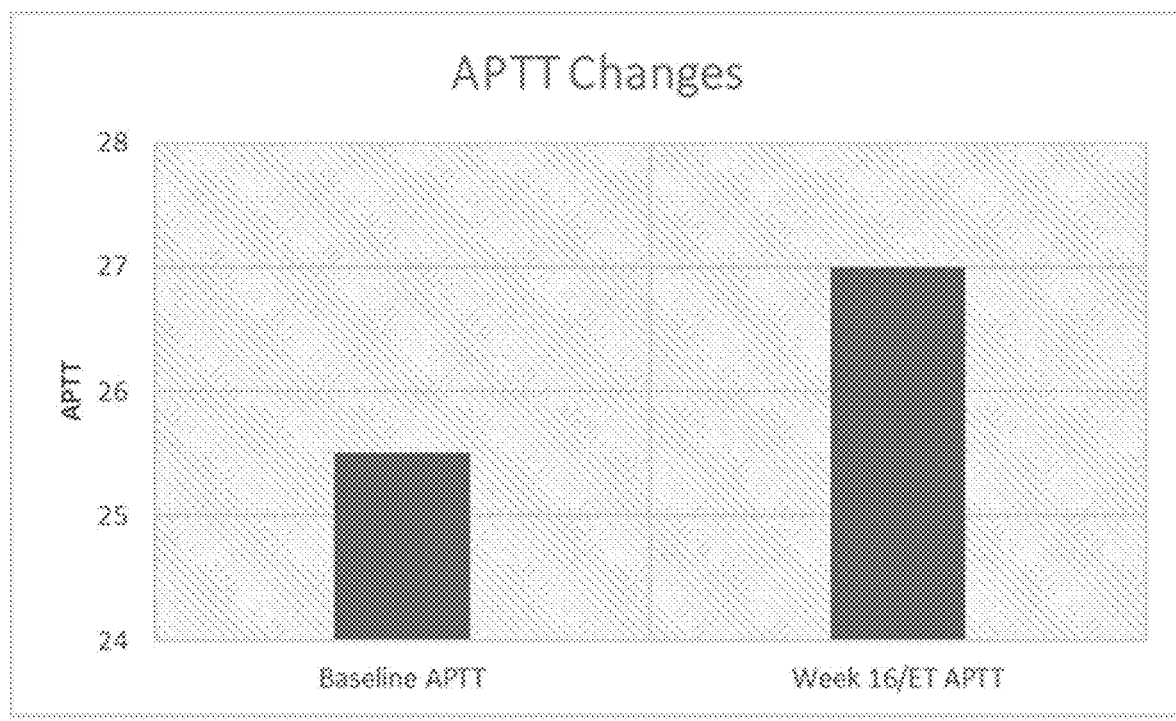
FIG. 2A shows activated prothrombin time (APTT) measured in Cushing's syndrome patients before and after receiving relacorilant. APTT measured after up to 16 weeks of relacorilant administration increased in these patients as compared to baseline APTT measurements.

FIG. 2A shows activated prothrombin time (APTT) measured in 12 Cushing's syndrome patients before and after receiving relacorilant. The APTT of Group 2 patients receiving relacorilant was measured at baseline (before relacorilant administration) and after 16 weeks (or following the last relacorilant administration for those patients who did receive the full 16 weeks of relacorilant administration). As shown in FIG. 2A, APTT increased significantly in this group following relacorilant administration (p-value: 0.014). Increased APTT indicates an increase in the time for blood coagulation; that is, a reduction in hypercoagulation. Thus, these results indicate that, for patients initially suffering from hypercoagulopathy (i.e., as in these Cushing's patients), the hypercagulopathy was reduced, and the risk of clotting disorders associated with hypercoagulopathy, such as DVT, PE, and VTE, are reduced.

Improvement/normalization of abnormally elevated coagulation factors caused by excess cortisol activity was observed as early as after one month of treatment with relacorilant. This is in contrast to what is observed after curative surgery for pituitary Cushing syndrome cases where coagulation factors start to decrease 3 months post-surgery and often remain elevated for at least 6 months post-surgery (Trementino et al., Neuroendocrinology 92 Suppl 1:55-59 (2010). Considering the high risk of thrombotic events in patients with active Cushing syndrome as well as following curative surgery, relacorilant might even be an option for pre-operative coagulation control of patients at high risk of peri-and post-operative thrombotic events.

Figure 2B:
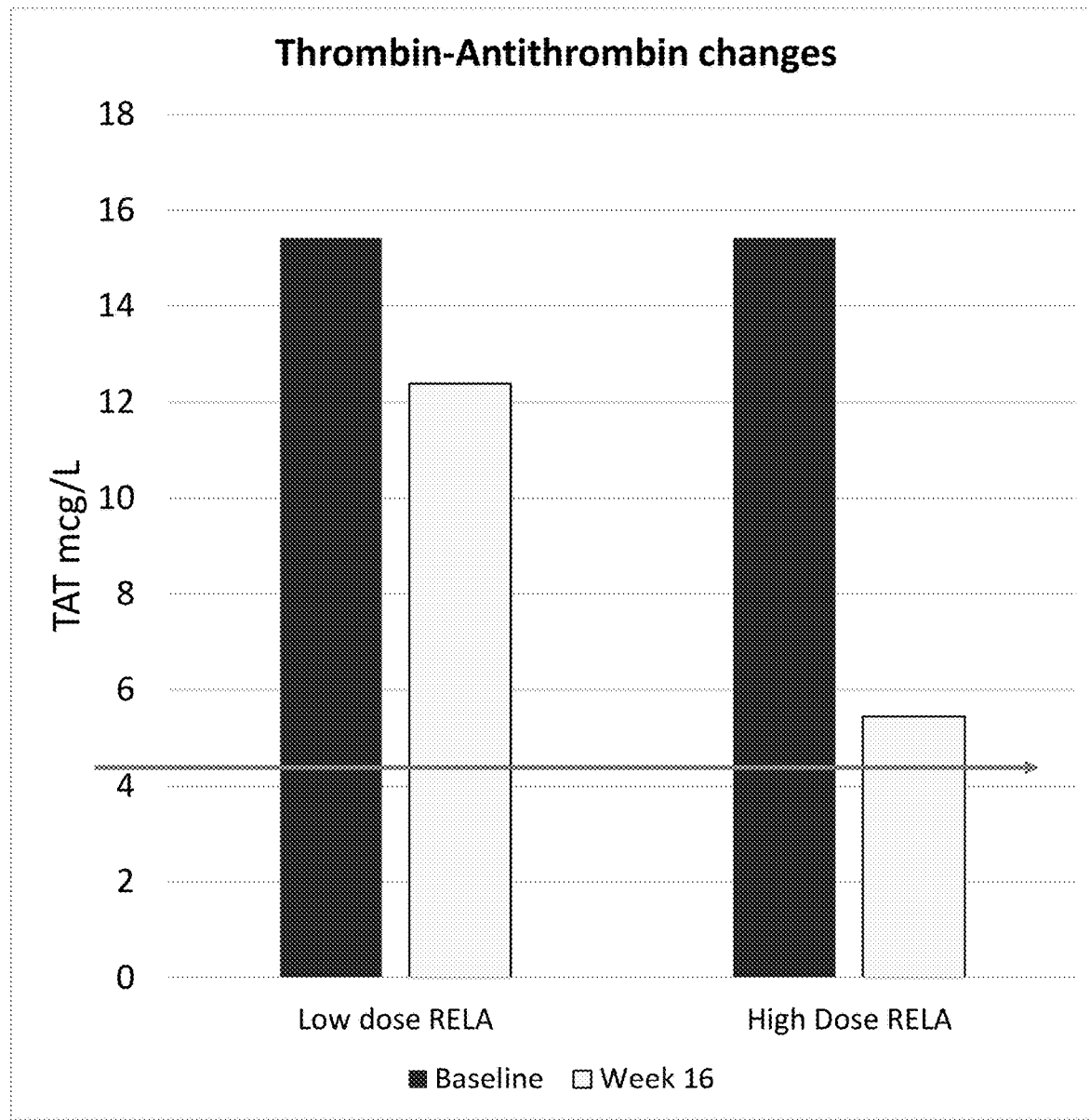
FIG. 2B Relacorilant effects on Coagulation: There is a high risk of thrombotic events in patients with Cushing's syndrome; Cushing's syndrome patients treated with relacorilant showed improvement in coagulation factors. This result indicates that relacorilant may be useful to improve pre-operative coagulation control (before surgery for Cushing's syndrome) in Cushing's syndrome patients at high risk of thrombotic events.

FIG. 2B shows the effects of relacorilant on coagulation factors (thrombin-antithrombin). The coagulation profile of the Cushing's patients treated with relacorilant was improved compared to baseline. Coagulation factors, and risk of disorders such as DVT, PE, and VTE, change after surgical treatment for Cushing's syndrome (e.g., after resection of a pituitary tumor in a patient suffering from Cushing's Disease). Factor VIII levels and von Willebrand Factor levels in Cushing's patients undergoing surgery were elevated before surgery (about 150% to 200% of normal), and increased one month after surgery. It took up to six months or more for these levels to be reduced to those that obtained prior to surgery; Factor VIII and von Willebrand Factor levels were improved at 12 months after surgery, to levels below about 125% of normal (Casonato, et al. Blood Coagulation and Fibrinolysis 10(3):145-151 (1999)).

Figure 1B:
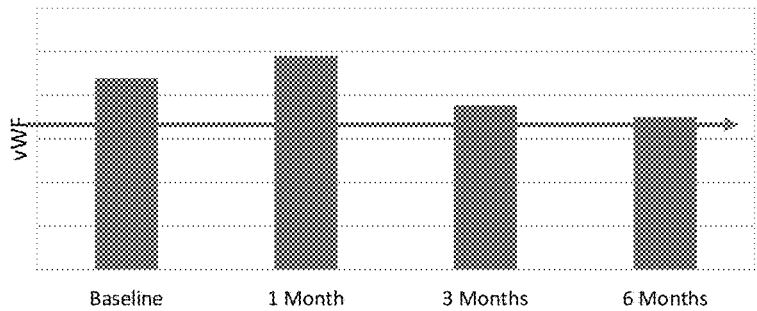
FIG. 1B shows von Willebrand Factor over time in Cushing's syndrome patients after surgery (top) and during treatment with relacorilant (bottom).
Figure 1B:
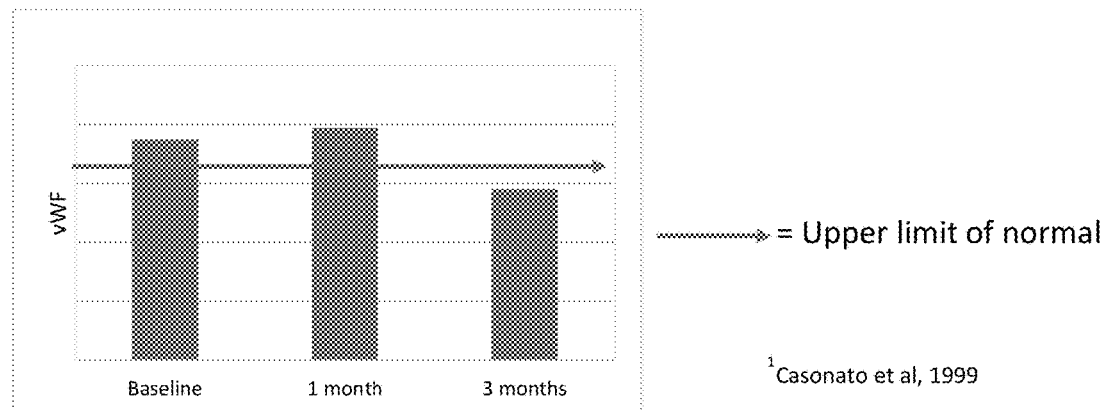
Figure 1C:
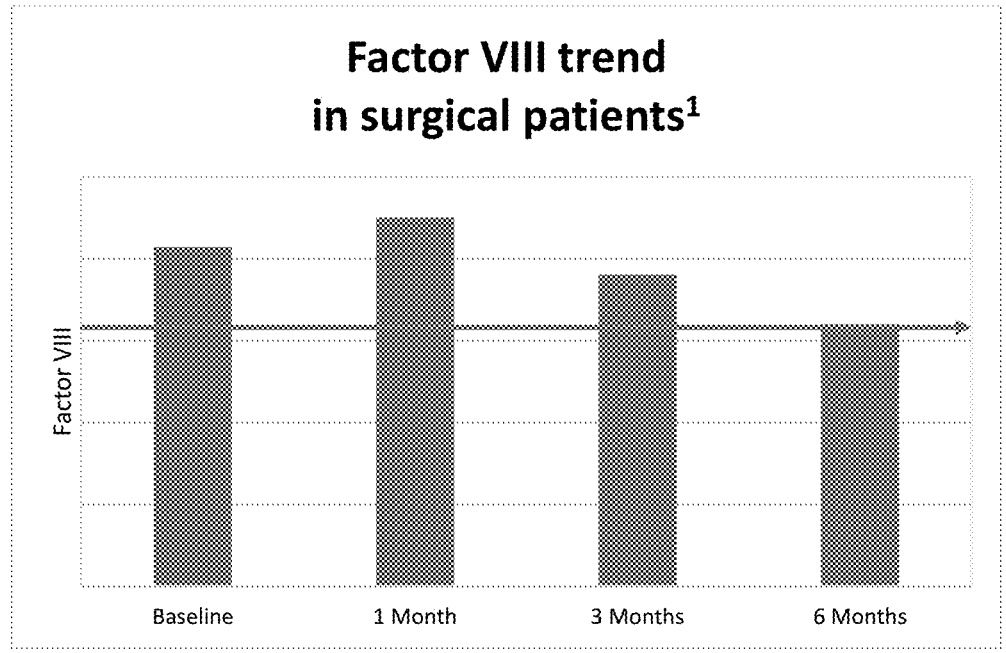
FIG. 1C shows Factor VIII over time in Cushing's syndrome patient after surgery (top) and during treatment with relacorilant (bottom). The data in the upper graph showing Factor VIII changes in surgical patients is from Casonato et al., 1999. The arrows indicate the upper limit of normal levels of Factor VIII.
Figure 1C:
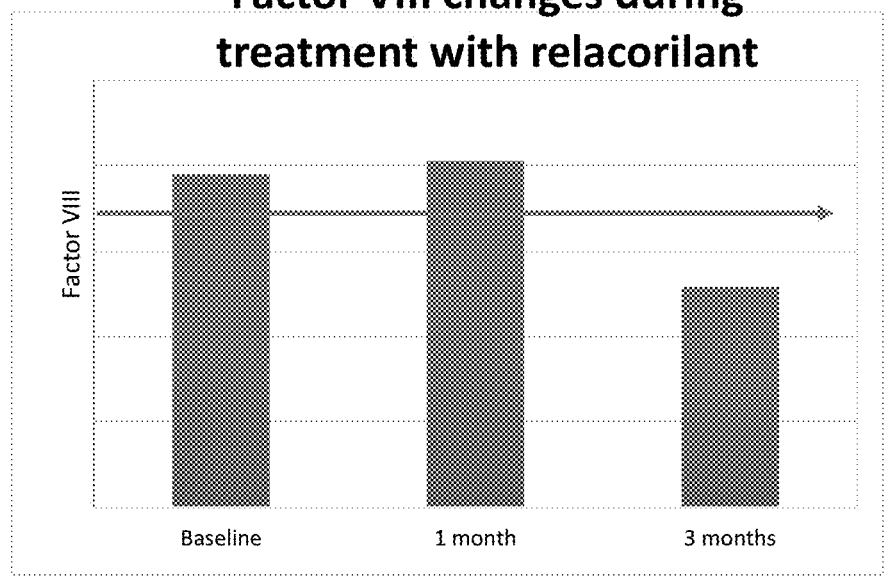

In contrast, as shown in FIGS. 1A, 1B, and 1C, neither Factor VIII or von Willebrand's Factor increased greatly with relacorilant administration. Moreover, Factor VIII levels declined after only 3 or 4 months of relacorilant treatment. In addition, as shown in FIG. 2, APTT measurements increased in Cushing's patients receiving relacorilant, indicating reduced risk of coagulation and reduced risk of DVT, PE, and VTE. These results show that relacorilant treatment improves the coagulation profile of Cushing's patients. These results further suggest that relacorilant treatment of Cushing's patients provides a better coagulation factor profile, earlier after treatment, than does surgery.

Figure 3:
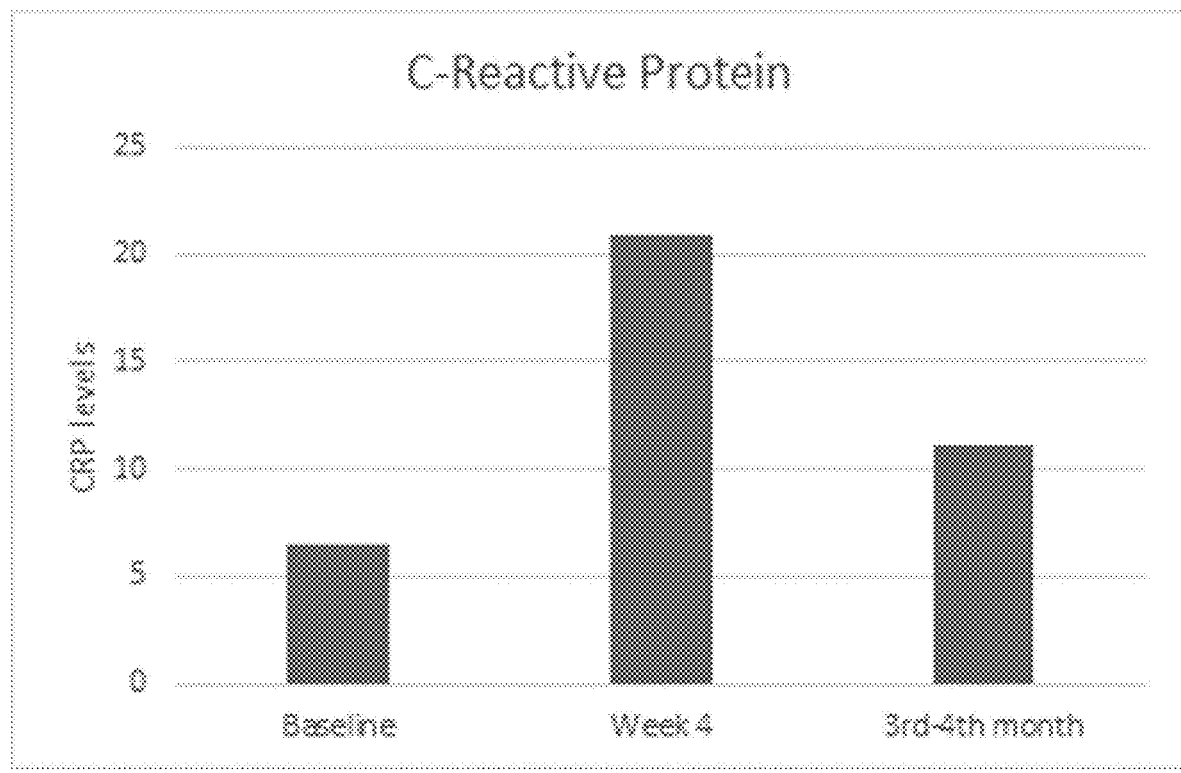
FIG. 3 shows C-Reactive protein levels over time in Cushing's syndrome patients treated with relacorilant. C-Reactive protein level is correlated with the level of inflammation in a patient. C-Reactive protein levels initially rise somewhat (at four weeks), and then return to baseline levels after 3 or 4 months of relacorilant treatment. These changes in C-Reactive protein levels are similar to those observed for Von Willebrand factor levels as well.

FIG. 3 shows C-Reactive protein levels over time in the Cushing's syndrome patients treated with relacorilant. C-Reactive protein level is correlated with the level of inflammation in a patient. C-Reactive protein levels initially rise somewhat (at four weeks), and then return to baseline levels after 3 or 4 months of relacorilant treatment. These changes in C-Reactive protein levels are similar to those observed for Von Willebrand factor levels as well. Thus, the changes in the inflammation marker C-Reactive protein are similar to those seen for coagulation factors.

Although the foregoing invention has been described in some detail by way of illustration and example for purposes of clarity of understanding, one of skill in the art will appreciate that certain changes and modifications may be practiced within the scope of the appended claims. In addition, each patent, patent publication, and reference cited herein is incorporated by reference in its entirety to the same extent as if each patent, patent publication, and reference was individually incorporated by reference.

I claim:

1. A method of treating hypercoagulopathy in a Cushing's syndrome patient, the method consisting of:
Identifying symptoms of hypercoagulopathy in a Cushing's syndrome patient, and
Administering to said patient an effective amount of relacorilant, which is (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, and which has the following structure:

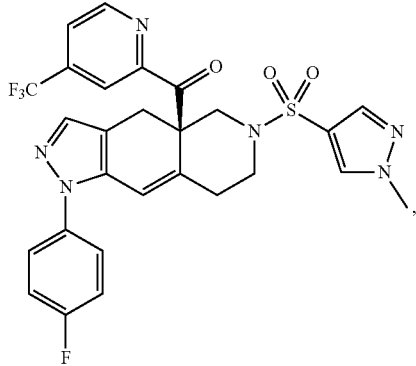 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

Whereby said hypercoagulopathy in said Cushing's syndrome patient is treated.

2. The method of claim 1, wherein said relacorilant is administered orally.

3. The method of claim 1, wherein the Cushing's syndrome patient suffers from Cushing's Disease.

4. The method of claim 1, wherein said effective amount of said relacorilant is a daily amount selected from 50 milligrams (mg), 100 mg, 150 mg, 200 mg, 250 mg, 300 mg, 350 mg, and 400 mg.

5. The method of claim 4, wherein said effective amount of said relacorilant is a once daily amount of relacorilant.

6. A method of treating deep vein thrombosis (DVT), pulmonary embolism (PE), or venous thromboembolism (VTE) in a Cushing's syndrome patient, the method consisting of:
Identifying symptoms of DVT, or PE, or VTE in a Cushing's syndrome patient, and
Administering to said patient an effective amount of relacorilant, which is (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, and which has the following structure:

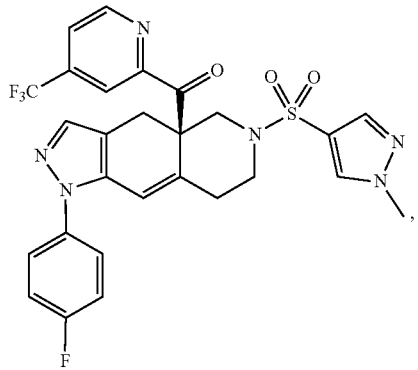 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

Whereby said DVT, PE, or VTE in said Cushing's syndrome patient is treated.

7. The method of claim 6, wherein said relacorilant is administered orally.

8. The method of claim 6, wherein the patient suffers from Cushing's Disease.

9. The method of claim 6, wherein said effective amount of said relacorilant is a daily amount selected from 50 milligrams (mg), 100 mg, 150 mg, 200 mg, 250 mg, 300 mg, 350 mg, and 400 mg.

10. The method of claim 9, wherein said effective amount of said relacorilant is a once daily amount of relacorilant.

* * * * *